United States Patent [19]

France et al.

[11] 4,184,978
[45] Jan. 22, 1980

[54] STABLE WATER IN OIL EMULSION SYSTEMS FOR COSMETIC AND PHARMACEUTICAL PREPARATIONS

[75] Inventors: James R. France, Overland Park; Fred Baiocchi, Prairie Village, both of Kans.; George A. Concar, Bloomingdale, Ill.

[73] Assignee: C. J. Patterson Company, Kansas City, Mo.

[21] Appl. No.: 861,362

[22] Filed: Dec. 16, 1977

Related U.S. Application Data

[63] Continuation-in-part of Ser. No. 793,534, May 4, 1977, abandoned.

[51] Int. Cl.$^2$ ............................................. B01J 13/00
[52] U.S. Cl. .................................... 252/309; 252/351; 252/356; 252/DIG. 17; 424/170; 424/172
[58] Field of Search ...................... 252/309, DIG. 17; 424/170, 172

[56] References Cited

U.S. PATENT DOCUMENTS

| | | | |
|---|---|---|---|
| 2,733,252 | 1/1956 | Thompson et al. | 260/410.9 Q |
| 2,744,825 | 5/1956 | Thompson et al. | 426/24 |
| 2,744,826 | 5/1956 | Thompson et al. | 426/622 |
| 2,789,992 | 4/1957 | Thompson et al. | 260/410.9 Q |
| 2,948,686 | 8/1960 | Gianladis | 252/309 X |
| 3,137,623 | 6/1964 | Gessler | 424/170 |
| 3,244,534 | 4/1966 | Buddemeyer et al. | 252/356 X |
| 3,770,855 | 11/1973 | Benson et al. | 252/DIG. 17 |

*Primary Examiner*—Richard D. Lovering
*Attorney, Agent, or Firm*—Schmidt, Johnson, Hovey & Williams

[57] ABSTRACT

A highly stable water in oil emulsion system for cosmetic or pharmaceutical preparations is provided wherein an unexpectedly high proportion of from about 70% to about 80% of an internal aqueous phase may be dispersed as globules usually of about one micron in a continuous external oleaginous phase by use of an emulsifier composition containing cooperatively effective amounts of (1) a di- or tri-valent salt of the esterification product of a $C_{10}$ to $C_{22}$ fatty acid with a hydroxy carboxylic acid containing 2 to 4 carbon atoms (preferably calcium stearoyl-2-lactylate), and (2) a co-emulsifier compatible with emulsion (1) having an HLB value and present in a quantity to cause said emulsifier composition to have an effective HLB value within the range of about 4.6 to about 6.6. An emulsion may be produced using simple mechanical mixing techniques which has a static shelf life of at leat about six months at approximately 25° C.

25 Claims, No Drawings

STABLE WATER IN OIL EMULSION SYSTEMS FOR COSMETIC AND PHARMACEUTICAL PREPARATIONS

CROSS REFERENCE

This application is a Continuation-In-Part of Application Ser. No. 793,534, filed May 4, 1977, of the same title, and now expressly abandoned.

This invention relates to stable water in oil emulsion systems especially useful in the cosmetic and pharmaceutical fields and involves the discovery that an unusually high proportion in the range of about 70% to about 80% of an aqueous internal phase may be dispersed in a continuous, liquid external oleaginous phase using a unique combination of emulsifiers which impart unexpected stability to the emulsion system.

Although a need for water-in-oil emulsions having a high water or aqueous phase content has long existed for use in pharmaceuticals and cosmetic and toiletry preparations such as night creams or barrier creams and lotions, moisturizing creams and lotions, sun screen creams and lotions and products such as make-up removers and skin cleansers, the industry has not heretofore been able to provide emulsion bases or carriers of the water-in-oil type where the aqueous phase exceeds 45% to 55% on a weight to weight basis. Although many benefits are to be derived from providing a high water content in water-in-oil emulsion systems for cosmetic applications in particular, formulators have not heretofore been able to add more than about 50% water to the emulsion without seriously affecting the shelf life stability of preparation using the emulsion system as a base. It is to be appreciated in this respect that because of the time delay that occurs between formulation of a product and retail sale, it is undesirable to employ an emulsion which will break in a short period of time, particularly when exposed to temperature extremes that are encountered during transportation and warehouse storage. Although stability under normal climatic conditions is an asset, at the very miniumum the emulsion system should be able to withstand temperatures of the order of 110° F. for at least six months without breaking.

Water-in-oil emulsions are used in barrier preparations or pore-occluding products to provide a thin oleaginous layer over the areas of the user's skin to which the composition is applied. Increasing the amount of water in the emulsion decreases the oily feel of the material without deleterious effects on the overall utility of the formulation and has greater customer appeal because the higher water content enhances the evaporative and thereby cooling effect of the cream or lotion upon application. Products formulated from the emulsion systems of this invention are less greasy and cooler upon application than prior creams and lotions while still retaining the emollient characteristics and occlusivity on the skin which are required in products of this type.

U.S. Pat. No. 2,948,686 to Gianladis describes water-in-oil emulsions but the patentee was not able to incorporate more than about 52% water in his emulsion system. In the dermatological products of U.S. Pat. No. 3,137,623 to Gessler, the maximum amount of water in the water-in-oil emulsions of this patent does not exceed about 10%. These are typical of the water ranges now employed in water-in-oil emulsion systems in commercial use.

It has now unexpectedly been discovered that much higher than anticipated quantities of water may be included in a water-in-oil emulsion within an unpredictably high range by using certain emulsifiers which are critical as to type and relative proportions necessary to give a required HLB value.

One supplier of emulsifiers has suggested that the mixture of the polyethylene ether of lanolin alcohol when used in conjunction with ethylene oxide-3-oleyl alcohol would permit incorporation of up to 82% water in a continuous oleaginous phase. Tests with this formulation however confirm that the resulting emulsion is unsatisfactory as a commercial base or carrier because of its short shelf life. A formulation of the type suggested gave the following results:

EXAMPLE 1

|    | INGREDIENTS | % W/W |
|----|---|---|
| A. | Oil Phase | |
|    | Polyethylene ether of lanolin alcohol | 1.0 |
|    | Ethylene oxide-3-oleyl alcohol | 3.0 |
|    | Mineral oil 65/75 S.S.U. | 14.0 |
| B. | Aqueous Phase | |
|    | Glycerine | 4.0 |
|    | Water (deionized) | 77.8 |
|    | Methyl paraben (as a preservative) | 0.2 |

PROCEDURE

The polyethylene ether of lanolin alcohol was warmed in the ethylene oxide-3-oleyl alcohol and mineral oil. The mixture was cooled to room temperature and the glycerine and water added with vigorous mechanical agitation. When placed in a cabinet maintained at a constant temperature of 43° C., syneresis (first sign of visually observable water droplets to the naked eye) occurred in about 24 hours and gross separation was evident within one week. At this accelerated shelf life test, stability was found to be far less than the required six months at room temperature (25° C.).

Although especially useful for cosmetic products the oil-in-water emulsions described herein may also be effectively used for pharmaceutical compositions such as topical ointments and creams and topical vehicles.

Acyl lactylates, particularly the esterification products of fatty acids with short chain hydroxy carboxylic acids have been used for a number of years in the food industry as dough conditioners and softeners and as oil-in-water emulsifiers in nondairy compositions such as coffee whiteners and vegetable oil based whipped toppings. The reaction product of fatty acids having 10 to 22 carbon atoms with a hydroxycarboxylic acid containing 2 to 4 carbon atoms and especially lactic and glycolic acid have now been found to have desirable utility for formulation of water-in-oil emulsion systems for cosmetic and pharmaceutical applications having unpredictably high internal aqueous phases not only because of the effectiveness thereof, but equally as imortant, by virtue of the known and demonstrated safety of these materials for food uses and thereby insuring their dermatological safety. The acyl glycolates and lactylates of most significant utility in this respect for cosmetics and pharmaceuticals have the generic formula:

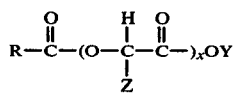

where

is the acyl radical of a fatty acid having from 10 to 22 carbon atoms, Z with H— or CH$_3$—, X is a number between 1 and 4, indicating the average number of glycolic or lactyl groups, and Y is a di- or tri-valent cation. The salts of the esterification product of a fatty acid with a hydroxy carboxylic acid (hereinafter generically referred to as FAEHC salts) described are anionic surface-active agents which exhibit an ability to complex with protein and starch systems. It has now been discovered that FAEHC salts of the defined structure when combined with a compatible co-emulsifier permit incorporation of theretofore difficult to obtain proportions of aqueous internal phases in a number of different types of continuous, external oleaginous phases. By use of preferred FAEHC salt emulsifiers combined with a co-emulsifier compatible with and cooperative to impart a specific HLB value to the emulsifier system, it has been unexpectedly found that water-in-oil emulsions may be prepared having a static shelf life in excess of six months at standard conditions of approximately 25° C. This unexpectedly long shelf life is obtained notwithstanding the fact that the amount of the aqueous discontinuous phase is exceptionally high and that the primary emulsifiers used in the system are completely safe and nontoxic, are wholly compatible with the user's skin, and in fact are synergistic in that they impart emollient and substantive skin characteristics to the composition not commonly found with other emulsions heretofore available for use in these fields.

In working with the preferred emulsion compositions as described and claimed herein, it was also discovered that the emulsion must have a minimum internal aqueous phase in the continuous oleaginous phase for maximum shelf stability. This minimum water content was unexpectedly found to be far higher though than heretofore even thought to be possible without substantially decreasing the shelf life of the emulsion at the temperatures encountered during marketing of formulation prepared therefrom. The minimum aqueous phase on a weight to weight percentage basis using the preferred emulsification agents disclosed herein was found to be from about 70% to about 80%. Examples which illustrate and confirm this discovery are as follows:

EXAMPLES 2 and 3

| | INGREDIENTS | % W/W | |
|---|---|---|---|
| A. | Oil Phase | (2) | (3) |
| | Mineral Oil 65/75 S.S.U. | 31.0 | 31.0 |
| | Calcium stearoyl-2-lactylate | 3.6 | 3.6 |
| | Polyethylene glycol (400) dioleate | 0.4 | |
| | Polyethylene glycol (400) dilaurate | | 0.4 |

-continued

| | INGREDIENTS | % W/W | |
|---|---|---|---|
| B. | Aqueous Phase | | |
| | Glycerine | 3.0 | 3.0 |
| | Water (deionized) | 61.8 | 61.8 |
| | Methyl paraben | 0.2 | 0.2 |

PROCEDURE

In each example, the ingredients of respective oil phases were combined and heated to 80° C. The aqueous phase ingredients were then separately combined and also heated to 80-85° C. The aqueous phases were then added to the corresponding oleagenous phases and mechanically agitated until room temperature was reached. The formulation of example 2 exhibited syneresis at least as early as the 21st day in a cabinet maintained at 43° C. while the example 3 composition commenced syneresis under the same conditions at about the 13th day. In both instances, the shelf life on the basis of room temperature conditions of 25° C. was less than six months.

As used herein, an emulsion is the combination of two immiscible liquids and an emulsifier composition made up of at least two compatible, mutually cooperative emulsifiers or surfactants. The emulsifiers found to be useful in preparing water-in-oil emulsion with high aqueous phase proportions have both hydrophilic and lipophilic properties. These compounds do not truly exist soley in either the aqueous or oleaginous phases but act as a connecting link between the minute aqueous globules dispersed in the continuous oil phase. Concentrating at the interface between the two immiscible phases, the molecules of the FAEHC salt surfactant are of necessity in spatial relationship determined by their steric configuration while the compatible co-emulsifier molecules may be considered as functioning between the lactylate molecules. In any event, where aqueous phases of about 70% up to about 80% on a weight to weight basis are dispersed in a continuous external oleaginous phase, exended static stability has heretofore been extremely difficult to obtain for any useful period of time (which for most products must at least be of the order of six months at standard conditions of 25° C.). This is believed to be in part attributable to the fact that at the high aqueous phase levels referred to, the aqueous medium globules are under such stress as to be distorted in form as opposed to a normal spherical configuration encountered at lower water levels and as a result, there is a great tendency for the particles to coalesce as they attempt to return to their more stable spherical configuration and this causes the emulsion to break rapidly.

It is, therefore, an important object of this invention to provide a water-in-oil emulsion system wherein from about 70% to about 80% on a weight to weight basis of an aqueous internal phase may be dispersed in an external continuous oleaginous phase by use of a unique emulsifier composition that imparts static stability to the emulsion for extended periods of time while at the same time exhibiting desirable cosmetic, toiletry and pharmaceutical characteristics with safe and non-toxic dermatological properties.

It is a further important object of the invention to provide an emulsion system as described wherein the emulsifier composition includes as a principal component an acyl lactylate which not only is especially effective to maintain an aqueous internal phase dispersed in an external oleaginous phase, but is especially desirable for use in this combination because the components of the emulsifier composition are like those which naturally occur as component parts of a person's skin. This enhances the safety and effectiveness of the cosmetic and pharmaceutical preparations.

A still further important object of the invention is to provide highly stable water-in-oil emulsion systems for cosmetics or pharmaceutical preparations which may be prepared using simple mechanical mixing techniques thus avoiding the necessity of subjecting the materials to homogenization while still obtaining unexpectedly long dispersion times exceeding at least 6 months under static conditions at a standard 25° C. temperature.

Another object of the invention is to provide emulsion systems as described for use in cosmetics, toiletries and pharmaceuticals which in preferred form utilize acyl lactylate emulsifiers which are readily available and that exhibit unusual safety since they have been demonstrated to be non-toxic not only on the skin but even when applied to the mucous membranes of the eyes.

Fatty acids and lactic acid are naturally occurring components of the skin's surface. Approximately 30% of the lipid material on the skin surface consists of free and combined fatty acids in more or less equal proportions. The fatty acids are straight chain monobasic acids containing between 8 and 20 carbon atoms. Lactic acid, a component of perspiration, is present as the free acid and as lactate. It is believed that lactic acid contributes to the skin's buffering capacity and may in fact add to the extensibility of the stratum corneum. It is extensibility which gives the stratum corneum its resistance to flaking and cracking, both symptoms of dry skin.

As a result of the discovery that certain acyl lactylates when used in conjunction with co-emulsifiers compatible therewith permit long life dispersion of aqueous internal phases in continuous external oleaginous phases, the possibility exists of preparing especially effective cosmetic, toiletry and pharmaceutical compositions. This is largely in part attributable to the fact that anionic acyl lactylate emulsifiers are perfectly suited for use in skin care and skin treatment products. It is also believed to in part be related to the fact that lactic acid and its salts as found naturally in the skin contribute to the skin's healthy environment by maintaining the proper pH and moisturization levels. Since acyl lactylate salts act as strong, effective anionic emulsifiers which are mild and not irritating to the skin, emulsions may readily be produced having enhanced emollient feel in creams and lotions and allowing the formulation of distinctive new products and modifications thereof with increased consumer appeal. The emolliency or substantive effect insofar as the skin is concerned, may be based on the protein complexing characteristics of the acyl lactylates which in conjunction with pH control, viscosity improving properties and ability to be used with a variety of other co-emulsifiers allow formulators a wide variety of prospective products, many of which are new in the field.

The fact that heretofore no more than about 45% to 55% on a weight to weight basis of an aqueous internal phase could be incorporated in a continuous oleaginous phase for use as an emulsion base in a cosmetic or pharmaceutical composition, may have been attributable to the fact that when other emulsifiers were employed, rapid coalescing of the aqueous globules occurred. Furthermore, safe, effective emulsifiers for use in dermatological applications were not generally available. It has now been discovered that a water-in-oil emulsion system may be prepared containing from about 70% to about 80% on a weight to weight basis of an aqueous internal phase dispersed in a continuous oleaginous carrier phase using the combination of a di- or tri-valent salt of the esterification product of a $C_{10}$ to $C_{22}$ fatty acid with a hydroxycarboxylic acid containing 2 to 4 carbon atoms and a co-emulsifier compatible with the cationic salt having an HLB value and present in a quantity to cause the emulsifier composition to have an effective HLB value within the range of about 4.6 to about 6.6. The preferred acyl lactylate is calcium stearoyl-2-lactylate which may be prepared in accordance with the procedures described in U.S. Pat. Nos. 2,733,252, 2,789,992, 2,744,825, and 2,744,826 which insofar as the disclosures thereof are relevant to the production of the lactylates described herein, are expressly incorporated by reference thereto. Calcium stearoyl-2-lactylate (CSL) has an acid value between 50 and 86, a calcium content of from 4.2% to 5.2%, an ester value between 125 and 164, and a total lactic acid concentration of between 32% and 38%. Dermatological tests have shown that CSL at 100% concentration has primary skin irritation index score of 0.0 and even at a much higher level than used is safe in eyes. In fact, as previously noted, CSL is essentially so non-toxic that it is approved for use in foods such as yeast leavened baked products, and dehydrated potatoes. The cited Patents also describe the preparation of useful glycolates, other di- or tri-valent salts of the esterification product of a fatty acid with a hydroxycarboxylic acid include calcium oleoyl lactylate, calcium isostearoyl lactylate, calcium stearoyl glycolate, magnesium stearoyl lactylate and aluminum stearoyl lactylate.

In preparing useful water-in-oil emulsions, a number of different oleaginous materials may be employed as the carrier compositions. For example, as an exemplary but not inclusive list, successful preparations may be based on the use of aliphatic oils such as mineral oil or petrolatum, fatty alcohols such as cetyl alcohol or stearyl alcohol, and natural or synthetic waxes which are soluble in liquid oil including beeswax, paraffin wax, carnauba wax, and Japan wax. The aqueous phase to be dispersed in the oleaginous medium is principally water but may include water soluble additives for lowering the freezing temperature of the overall composition or for other functional properties. Exemplary, but again nonexclusive constituents useful for this purpose are low molecular weight, water soluble polyoyls such as propylene glycol, glycerin, sorbitol and hexylene glycol, water soluble carbohydrates such as sucrose and dextrose, and water soluble inorganic salts in the nature of sodium chloride and potassium chloride. Finally, mention should also be made of the fact that most toiletry and cosmetic formulations include additives such as perfumes and preservatives which are introduced q.s. and the emulsifier composition must allow incorporation of these conventional substances into the formulation without adversely affecting the stability of the material. Similarly, pharmaceutical preparations must permit introduction of therapeutic agents into the topical material without changing the emulsion characteristics of the composition. In addition, the emulsion must be useful in a relatively wide pH range of about 3.5 to 10 without breaking of the emulsion.

The co-emulsifier used in conjunction with the principal FAECH salt emulsifier must be compatible therewith and have an HLB value which when combined with the primary surfactant salt gives an HLB within a relatively narrow range. Specifically, it has been determined that the useful HLB range is from about 4.6 to about 6.6 (noting in this respect that CSL, for example, has an HLB of about 5.1). In addition, the co-emulsifier desirably is a reaction product of a fatty acid to render the same fully compatible with the FAECH salt, assure non-toxicity thereof and to complement the stearic configuration of the primary emulsifier. Best results are obtained, though, if the fatty acid radical of the co-emulsifier is different from the fatty acid of the FAECH salt. Useful co-emulsifiers for water-in-oil emulsions employing the defined FAECH salts as the principal emulsifier constituent include but are not limited to polyethylene glycol derivatives of fatty acids such as polyethylene glycol (200) mono-oleate, polyethylene glycol (200) monolaurate, polyethylene glycol (400) dioleate, and polyethylene glycol (400) dilaurate. Ethylene oxide-3-oleyl alcohol may be used or in the alternative, sodium isostearoyl lactylate or a phosphated oleyl ether which has been neutralized such as diethanolamine-oleth-3-phosphate. In all instances, the coemulsifier should have an HLB value greater than the FAECH salt and when combined therewith give an effective HLB value within the specified range. In this respect, it is to be understood that when two or more surfactants are blended, if X is the proportion of one surfactant having an HLB of A and the other surfactant has an HLB of B, the HLB of the combination can be expressed for all practical purposes as $XA+(1-X)B$. This is essentially a straight line relationship. Using this formula, the amount of co-emulsifier to be combined with the defined FAECH salt may be readily determined recalling that the resulting HLB value should be within the range of about 4.6 to 6.6.

In most instances, it has been found that the greater the proportion of the FAECH salt with respect to the co-emulsifier the better the results, with best results obtained where the ratio is from about 50:50 to 90:10 and the preferred ratio being about 9 parts of the FAECH salt to 1 part of the co-emulsifier. A useful standard is to require that the emulsifier composition contain constituents which in combination impart adequate stability to the water-in-oil emulsion such that full dispersion thereof is maintained under static conditions for at least 6 months at a standard temperature of about 25° C. The aqueous phase may comprise from about 70% to about 80% on a weight to weight basis with respect to the external continuous oleaginous phase, but in most instances, the aqueous phase will be within the range of about 73% to 81%. In the case of an 81% aqueous phase, the oleaginous phase will comprise about 9% to 15% of the total composition on a weight to weight basis, while 4% to 10% of the emulsifier composition is added to the formulation to assure stability for the required 6 month period.

Useful water in oil emulsion systems prepared in accordance with the preferred concepts of the present invention include -

EXAMPLE 4 (Lotion)

| | INGREDIENTS | % W/W |
|---|---|---|
| A. | Oil Phase | |
| | Mineral Oil 65/75 S.S.U. | 23.0 |
| | Calcium stearoyl-2 lactylate | 3.6 |
| | Polyethylene glycol (200) monolaurate | 0.4 |
| B. | Aqueous Phase | |
| | Glycerine | 3.0 |
| | Water (deionized) | 68.8 |
| | Preservatives | 0.2 |

PROCEDURE

1. Combine A and heat to 80° C.
2. Combine B and heat to 80° to 85° C.
3. Add B to A while stirring and continue to stir until room temperature is reached.

EXAMPLE 5 (Lotion)

| | INGREDIENTS | % W/W |
|---|---|---|
| A. | Oil Phase | |
| | Mineral Oil 65/75 S.S.U. | 15.0 |
| | Calcium stearoyl-2 lactylate | 3.6 |
| | Ethylene oxide-3-oleyl alcohol | 0.4 |
| B. | Aqueous Phase | |
| | Glycerine | 3.0 |
| | Water (deionized) | 78.0 |

PROCEDURE

Same as EXAMPLE 4

EXAMPLE 6 (Lotion)

| | INGREDIENTS | % W/W |
|---|---|---|
| A. | Oil Phase | |
| | Mineral Oil 65/75 S.S.U. | 15.0 |
| | Calcium stearoyl-2 lactylate | 3.6 |
| | Sodium isostearoyl lactylate | 0.4 |
| B. | Aqueous Phase | |
| | Glycerine | 3.0 |
| | Water (deionized) | 78.0 |

PROCEDURE

Same as EXAMPLE 4

EXAMPLES 7 and 8

| | INGREDIENTS | % W/W | |
|---|---|---|---|
| | | (7) | (8) |
| A. | Oil Phase | | |
| | Mineral Oil 65/75 S.S.U. | 27.0 | 22.0 |
| | Calcium stearoyl-2-lactylate | 3.6 | 3.6 |
| | Polyethylene glycol (400) dioleate | 0.4 | 0.4 |
| B. | Aqueous Phase | | |
| | Glycerine | 3.0 | 3.0 |
| | Water (deionized) | 65.8 | 70.8 |
| | Methyl paraben | 0.2 | 0.2 |

PROCEDURE

Same as EXAMPLE 4

Stability tests on the above formulas showed that Nos. 4, 6, 7 and 8 remained stable for 22 days at 50° C. under static test conditions, which is equivalent to at least 6 months at a room temperature of 25° C., while the formulation of EXAMPLE 5 remained fully dispersed for sixteen days at 60° C. which is equivalent to at least 18 months static stability at a room temperature of 25° C.

Tests 9 and 10 set forth hereunder demonstrate the criticality of using the defined lactylate emulsifiers in conjunction with the stipulated co-emulsifiers:

EXAMPLES 9 and 10

| INGREDIENTS | | % W/W | |
|---|---|---|---|
| A. | Oil Phase | (9) | (10) |
| | Mineral Oil 65/75 S.S.U. | 23.0 | 23.0 |
| | Sodium stearoyl-2-lactylate | 3.0 | |
| | Calcium stearoyl-2-lactylate | | 3.0 |
| | Polyethylene glycol (200) dioleate | 1.0 | 1.0 |
| B. | Aqueous Phase | | |
| | Glycerine | 3.0 | 3.0 |
| | Water (deionized) | 69.8 | 69.8 |
| | Methyl paraben | 0.2 | 0.2 |

PROCEDURE

Same as EXAMPLE 4

Examples 9 and 10 were both found to exhibit syneresis when placed in 50° C. cabinets commencing at about 3 days following initiation of the tests thus confirming that they would not be stable for at least 6 months at 25° C. (or room temperature).

Although the amount of the emulsifier composition is used in the formulations will vary from application to application, best results are obtained with the FAECH salt as described when combined with the exemplary co-emulsifiers at total level of about 4% on a weight to weight basis. However, useful results are obtained when the emulsifier composition is maintained within the range of about 3% to 10% on a weight to weight basis.

One especially important feature of the emulsion systems of this invention is the fact that unusually stable preparations may be formulated using simple mixing techniques with mixers of the high shear type. In this way, additional, mechanical homogenization of the formulation is avoided notwithstanding the fact that the aqueous phase is broken up into individual globules of about one micron which resist coalescing for extended periods of at least six months under standard conditions. In addition, the emulsion system is capable of undergoing at least one freeze-thaw cycle and in most instances has been found to remain fully dispersed through two distinct freeze-thaw cycles, particularly when a polyol is included in the composition as an anti-freeze agent.

Having thus described the invention, what is claimed as new and desired to be secured by Letters Patent is:

1. A stable water-in-oil emulsion system for cosmetic and pharmaceutical preparations comprising:
   a substantially continuous, external liquid oleaginous phase;
   a liquid non-homogenized internal aqueous phase comprising a sufficient amount of small aqueous globules dispersed in said external phase to present a collective quantity thereof initially of the order of about one micron in size at the time of dispersion and present within the range of from about 70% to about 80% on a weight to weight basis of the two phases; and
   an emulsifier composition combined with said phases which is capable of maintaining the water dispersed in the oleaginous phase for an extended period and comprising cooperatively effective amounts of at least (1) a di- or tri-valent salt of the esterification product of a $C_{10}$ to $C_{22}$ fatty acid with a hydroxycarboxylic acid containing 2 to 4 carbon atoms and (2) a co-emulsifier non-reactive and compatible with emulsifier (1) said co-emulsifier being a derivative of a fatty acid or fatty alcohol which is different from the fatty acid radical of emulsifier (1) and having an HLB value and present in a quantity to (a) cause said emulsifier composition to have an effective HLB value within the range of about 4.6 to about 6.6 and (b) assure that the internal aqueous phase remains dispersed in said external phase for at least 6 months at approximately 25° C.

2. An emulsion system as set forth in claim 1 wherein emulsifier (1) is a di- or tri-valent salt of the esterification product of a $C_{10}$ to $C_{22}$ fatty acid with lactic acid.

3. An emulsion system as set forth in claim 2 wherein said fatty acid is stearic acid.

4. An emulsion system as set forth in claim 2 wherein emulsifier (1) is calcium stearoyl-2-lactylate.

5. An emulsion system as set forth in claim 1 wherein said co-emulsifier is a derivative of oleic acid or oleyl alcohol.

6. An emulsion system as set forth in claim 5 wherein said co-emulsifier is a polyethylene glycol or polyethylene oxide derivative of oleic acid or oleyl alcohol.

7. An emulsion system as set forth in claim 1 wherein said co-emulsifier is a derivative of lauric acid or lauryl alcohol.

8. An emulsifier system as set forth in claim 7 wherein said co-emulsifier is a polyethylene glycol or polyethylene oxide derivative of lauric acid or lauryl alcohol.

9. An emulsion system as set forth in claim 1 wherein said co-emulsifier is a metal salt of isostearoyl lactylate.

10. An emulsion system as set forth in claim 1 wherein the ratio of emulsifier (1) to emulsifier (2) is within the range of about 50:50 to about 90:10.

11. An emulsion system as set forth in claim 1 wherein said aqueous phase contains a water soluble polyol.

12. An emulsion system as set forth in claim 1 wherein said aqueous phase contains a water soluble carbohydrate.

13. An emulsion system as set forth in claim 1 wherein said aqueous phase contains a water soluble inorganic salt.

14. An emulsion system as set forth in claim 1 wherein said oleaginous phase is an aliphatic oil.

15. An emulsion system as set forth in claim 14 wherein said oil is mineral oil.

16. An emulsion system as set forth in claim 15 wherein said oil is petrolatum.

17. An emulsion system as set forth in claim 1 wherein said oleaginous phase is a fatty alcohol.

18. An emulsion system as set forth in claim 17 wherein said fatty alcohol is cetyl alcohol.

19. An emulsion system as set forth in claim 17 wherein said fatty alcohol is a stearyl alcohol.

20. An emulsion system as set forth in claim 1 wherein said oleaginous phase includes a wax which is soluble in a liquid oil.

21. An emulsion system as set forth in claim 1 wherein is included at least about 4% on a weight to weight basis of said emulsifier composition.

22. An emulsion system as set forth in claim 1 wherein said aqueous phase includes from 73% to 81% water on a weight to weight basis.

23. An emulsion system as set forth in claim 1 wherein said emulsifier (1) is calcium stearoyl-2-lactylate and there is provided at least 81% water in said aqueous phase, about 9% to 15% oil in said oleaginous phase, and about 4% to 10% of said emulsifier composition, all on a weight to weight basis.

24. A stable water-in-oil emulsion system for cosmetic and pharmaceutical preparations comprising:
   a substantially continuous, external liquid oleaginous phase;
   a liquid non-homogenized internal aqueous phase comprising a sufficient amount of small aqueous globules dispersed in said external phase to present a collective quantity thereof initially of the order of about one micron in size at the range of from about 70% to about 80% on a weight to weight basis of the two phases; and
   an emulsifier composition combined with said phases which is capable of maintaining the water dispersed in the oleaginous phase for an extended period and comprising cooperatively effective amounts of at least (1) a di- or tri-valent salt of the esterification product of a $C_{10}$ to $C_{22}$ fatty acid with a hydroxycarboxylic acid containing 2 to 4 carbon atoms and (2) a phosphated oleyl ether which has been substantially neutralized.

25. An emulsion system as set forth in claim 24 wherein said oleyl ether is diethanolamine-oleth-3-phosphate.